United States Patent [19]
Jacobson et al.

[11] Patent Number: 4,711,852
[45] Date of Patent: Dec. 8, 1987

[54] CONTROL FOR BLOOD GAS ANALYZERS AND HEMOGLOBIN ANALYSIS

[75] Inventors: Walter Jacobson, Denville; Stephen C. Riggio, Milford; James E. Turner, Boonton, all of N.J.

[73] Assignee: Akzo N.V., Arnhem, Netherlands

[21] Appl. No.: 667,947

[22] Filed: Nov. 5, 1984

[51] Int. Cl.$^4$ .............................................. G01N 31/00
[52] U.S. Cl. ........................................ 436/15; 436/16; 436/8; 436/11
[58] Field of Search ................ 436/11, 15, 18; 424/2, 424/3; 435/2; 252/408.1

[56] References Cited

U.S. PATENT DOCUMENTS

| | | | |
|---|---|---|---|
| 3,859,049 | 1/1975 | Ware et al. | 436/11 |
| 3,973,913 | 8/1976 | Louderback | 436/11 |
| 4,405,719 | 9/1983 | Crews et al. | 436/18 |
| 4,485,174 | 11/1984 | Chiang et al. | 436/18 |
| 4,521,518 | 6/1985 | Carter et al. | 436/15 |

OTHER PUBLICATIONS

Niehaus, W. G., et al, "Cross-Linking of Erythrocyte Membranes with Dimethyl Adipimidate," Biochim. Biophys. Acta 196:170–175 (1970).
Lubin, B. H., et al, "Dimethyl Adipimidate: A New Antisickling Agent", Proc. Nat. Acad. Sci U.S.A., vol. 72, No. 1, pp. 43–46, Jan. 1975.
Waterman, M. R., et al, "Antisickling Nature of Dimethyl Adipimidate, " Biochem. Biophys. Res. Comm., vol. 63:No. 3, 580–587 (1975).
Krinsky, N. I., et al, "Retention of K+ Gradients in Imidoester Cross-Linded Erythrocyte Membranes,: Arch. Biochem. Biophys., 160 350–352 (1974).

Primary Examiner—Deborah L. Kyle
Assistant Examiner—T. J. Wallen
Attorney, Agent, or Firm—William M. Blackstone

[57] ABSTRACT

A blood gas-hemoglobin analysis control which simulates whole human blood characteristics comprising a buffered suspension medium containing erythrocytes which have been stabilized with an imidoester protein cross-linking agent while being contacted with a gas consisting of pure oxygen or pure carbon monoxide.

22 Claims, No Drawings

CONTROL FOR BLOOD GAS ANALYZERS AND HEMOGLOBIN ANALYSIS

BACKGROUND OF THE INVENTION

Blood gas analyses are performed in most hospital laboratories for the purpose of diagnosing and treating abnormalities of pulmonary function and acid/base balances. The three parameters measured are blood pH, $CO_2$ partial pressure ($P_{CO_2}$), and oxygen partial pressure ($P_{O_2}$). Additionally, hemoglobin tests may also be performed. These tests include the determination of total deoxyhemoglobin, oxyhemoglobin, carboxyhemoglobin and methemoglobin.

In performing the pH, $P_{O_2}$ and $P_{CO_2}$, tests a blood sample is drawn from the patient and introduced into specialized equipment containing electrodes which are specific for the parameter to be measured. Since blood deteriorates rapidly and dissolved gases tend to come out of solution, it must be analyzed promptly, or within a few hours if the blood has been cooled on ice.

It is, of course, axiomatic that the test results can be no better than the instrumentation used. Therefore, it is necessary to monitor the equipment for proper calibration and function. While an extraneous gas source can be used to standardize blood gas control equipment, the electrodes used in testing are sensitive to the test medium. For example when oxygen in the gaseous state is used as the standard, an instrument reading is obtained which is different from that obtained when the standard is a liquid containing dissolved oxygen. This liquid-gas difference is a result of differences in rates of diffusion of oxygen through the gaseous or liquid medium with which it is associated.

In order to alleviate the need for mathematical corrections to compensate for this liquid-gas difference, it has been recognized that a liquid control is preferred to a gaseous control. The preferred liquid would, of course, be blood since it comprises all of the constituents to which the test instrument is exposed. Blood, however, deteriorates rapidly and loses dissolved gases. In addition, as a result of cellular metabolism, $P_{CO_2}$ increases while $P_{O_2}$ and pH decrease. Since there is no recognized process for preventing these changes from occurring in stored whole blood, it has been rejected as a control.

The first liquid blood gas controls were buffered water solutions containing dissolved gases. While these solutions avoided the liquid-gas difference problem, they lacked other components of blood which effect the sensitive electrode components of the test equipment.

As a first step in resolving that problem, controls were prepared which contained soluble hemoglobin. These controls, however, lacked the methemoglobin reductase enzyme which, in the blood cell, reduces iron to the $Fe^{++}$ state. As a consequence the iron of the hemoglobin is always in the $Fe^{+++}$ state, that is, the hemoglobin is themoglobin. Hence, these controls can only be used for total hemoglobin analyses. More recently, controls have been developed which more closely approximate whole blood.

U.S. Pat. No. 3,859,049 teaches a method for stabilizing whole blood and whole blood components utilizing fluorides, citrates, fluoroacetic acid and iodoacetic acid. Typically, sodium fluoride, sodium citrate, and fluoroacetic or iodoacetic acid are added to whole blood. The mixture is refrigerated and allowed to age for a period sufficient to stabilize $P_{CO_2}$, $P_{O_2}$ and pH levels. Unfortunately, the product has a short shelf life of about one month. A product with a longer shelf life has been prepared by treating the blood components with an aldehyde.

U.S. Pat. No. 3,973,913 teaches a method for stabilizing red blood cells by separating them from whole blood and stabilizing them by treatment with an aldehyde, e.g., formaldehyde or glutaraldehyde. These stabilized cells are added to a buffered solution containing glucose, neomycin and chloramphenicol as bactericides, and salt to provide an isotonic solution which has an osmolality similar to that of blood. This product has a shelf life of only two months, however, and the cells rapidly lose hemoglobin which is oxidized to methemoglobin.

What is needed is an improved stabilizing technique which will result in more stable blood gas and hemoglobin analysis controls which simulate whole blood.

As used in the specification and claims, the term "hemoglobin analysis" means those hemoglobin tests which measure total hemoglobin, percent oxyhemoglobin, percent carboxyhemoglobin and percent methemoglobin. Other parameters such as volume % $O_2$ and $CO_2$ can be calculated from the observed values.

Dimethyl adipimidate has been disclosed as a cross linking agent for erythrocyte membranes; see Niehaus, W.G., et al. "Cross-Linking of Erythrocyte Membranes With Dimethyl Adipimidate," *Biochem. Biophys. Acta* 196: 170–175 (1970).

In other studies dimethyl adipimidate (DMA) has been disclosed as being an antisickling agent for red blood cells; see "Dimethyl Adipimidate: A New Antisickling Agent," Lubin, B.H., et al., *Proc. Nat. Acad. Sci. U.S.A.*, Vol. 72, No. 1 pp 43–46, Jan. 1975 and "Antisickling Nature of Dimethyl Adipimidate," Waterman, M. R. et al, *Biochem Biophys. Res. Comm.*, Vol. 63: No. 3, 580–587 (1975).

More recently the cross-linking effects of DMA have been shown to inhibit enzyme activity; see "The Effect of Crosslinking Reagents on Red-Cell Shape," Mentzer, W. C. and Lubin, B. H., *Seminars in Hematology* 16:115–127 (April 1979). Additionally, DMA has been shown to affect ion retention in erythrocytes. Krinsky, N. I., et al. "Retention of $K^+$ Gradients in Imidoester Crosslinked Erythrocyte Membranes," *Arch. Biochem. Biophys.*, 160, 350–352 (1974).

No application of DMA cross-linking of erythrocyte membranes to blood gas controls is disclosed in the prior art.

SUMMARY OF THE INVENTION

It has surprisingly been found that a blood gas-hemoglobin analysis control can be prepared by stabilizing red blood cells with dimethyl adipimidate (DMA) and suspending the stabilized cells in a buffered medium which can contain a protein to simulate the effect of plasma protein on blood gas measurements. The preferred plasma protein is bovine serum albumin.

By separately treating red cells with oxygen or carbon monoxide during the DMA cross-linking phase, controls can be prepared for use in hemoglobin determinations. The buffered red-cell suspension is packaged in ampules and stored under refrigeration. The preferred buffering agents are N-(Tris-hydroxymethyl)methyl-2-aminoethanesulfonic acid (TES) or N-2-Hydroxyethyl-piperazine-N-2-ethanesulfonic acid (HEPES).

DETAILED DESCRIPTION

This invention relates to a control which can be used in both blood gas and hemoglobin determinations. More particularly, it relates to a control which comprises stabilized erythrocytes suspended in a buffered medium. In the practice of this invention any erythrocytes of mammalian origin can be used. However, the preferred erythrocytes are human erythrocytes.

The control of this invention can be prepared with discrete levels of each of the experimentally determined parameters, i.e., pH, $P_{O_2}$, $P_{CO_2}$, total hemoglobin concentration (THb), percent oxyhemoglobin ($O_2$ Hb), percent carboxyhemoglobin (COHb), and percent methemoglobin (MetHb). Thus, each of these parameters can be selected to simulate clinical acidosis, normalcy and alkalosis on either a metabolic or respiratory basis. The parameter ranges over which a control can be prepared are:

| Parameter | Range | Preferred Range | Most Preferred Range |
|---|---|---|---|
| pH | 6.6 to 8.0 | 6.8 to 7.8 | 7.0 to 7.7 |
| $P_{O_2}$ mmHg | 20 to 200 | 30–180 | 40–150 |
| $P_{CO_2}$ mmHg | 10 to 150 | 15–75 | 15–65 |
| THb, g/dl | 3 to 24 | 5–21 | 9–17 |
| % $O_2$Hb, % | 0 to 100 | 50–100 | 60–98 |
| % COHb, % | 0 to 100 | 0–50 | 0–35 |
| % MetHb, % | 0 to 30 | 0–10 | <3 |

A typical range of parameter concentrations is pH, about 6.8 to about 8.0; total hemoglobin about 3 to about 24 g/dl; oxyhemoglobin, about 60–100%; carboxyhemoglobin, about 0–35% and methemoglobin, less than 3%. These ranges are selected because they approximate the physiologically encountered ranges of these parameters.

Erythrocytes from freshly drawn blood as well as erythrocytes from aged blood, e.g., blood cells aged for up to 11 weeks, can be used. Greater stability can be achieved using aged cells. Preferably, blood cells are aged at least six weeks; more preferably, at least ten weeks.

In preparing the control of this invention erythrocytes are stabilized by reaction with DMA and suspended in a buffered medium. Four criteria govern the selection of the buffer suitable for use in the practice of this invention:

1. It must have sufficient buffer capacity over the pH range of interest.
2. It must be characterized by a pH vs. temperature coefficient which adequately simulates that of fresh whole blood.
3. It must be usable in a concentration which is adequate to ensure stability of the pH and yet afford sufficient sensitivity for detecting sources of error in the pH measuring systems.
4. It must not adversely affect the erythrocytes.

It will be apparent to those skilled in the art that a wide range of buffers meet these criteria. As used in the specification and claims, the term "buffering agent" means a buffer compound which meets the foregoing criteria.

Illustrative, non-limiting examples of buffers suitable for use in the practice of this invention are N-(Trishydroxymethyl) methyl-2-aminoethanesulfonic acid (TES) and N-2-Hydroxyethylpiperazine-N-2-ethanesulfonic acid (HEPES). The buffer is used at concentrations of about 0.01 to about 0.10 M.; preferably, about 0.025 to about 0.09 M; more preferably, about 0.035 to about 0.08 M; most preferably about 0.05 to about 0.07 M.

The correct operation of a pH meter and blood gas equipment requires good control of the temperature at which the measurements are performed. In order to simulate the performance of whole blood in the thermostated system it is desirable to have a control which has a pH vs. temperature coefficient which is equal to that of whole blood (−0.015 pH units/°C). Therefore the pH vs. temperature coefficient of the reference control of this invention is preferably at least −0.015 pH units/°C.

A control using HEPES as the buffering agent at a concentration of about 0.05 to about 0.07 M has a pH vs. temperature coefficient of −0.015 pH/°C.

In the preparation of the control of this invention the stabilized erythrocytes are suspended in a liquid buffered medium which can be a deionized water solution of the buffering agent. However, in blood gas measurements the determinations can be affected by plasma proteins as a result of coating of the electrodes. This effect can be simulated by incorporating into the buffered liquid suspension medium a protein which does not (1) form a precipitate, (2) cause fibrin clots or (3) cause agglutination of the erythrocytes. Further, the protein must not be contaminated with residual enzymes which would affect the stability of the control.

The protein concentration of human plasma is about 4.0–6.0% w/v. A suitable standard can be prepared using a protein concentration of about 0.4 to 8.0% w/v. Below 0.4% no substantial coating effect is observed while above 8.0% w/v the coating effect is in excess of that which can ordinarily be anticipated with a human blood sample. The protein concentration utilized in the preparation of the controls of this invention is preferably about 2% to about 7% w/v; more preferably about 3% to about 6.5% w/v; most preferably 4.0–6.0% w/v. Any inert, water soluble protein may be used as a source of protein for the controls of this invention. As used with respect to those proteins, the term "inert" means that the proteins will not degrade the erthrocyte or otherwise cause it to deteriorate. Hence, enzymes are generally not a suitable source of such proteins.

While mammalian serum albumins generally are suitable sources of protein for the controls of this invention, the preferred serum albumins are human serum albumin and bovine serum albumin. Bovine serum albumin is most preferred since it is readily available in a purified form at a reasonable cost. Alternatively, gelatin may be used as the protein.

It will be evident to those skilled in the art that any of the prior art blood gas controls can be improved and made to be more similar to whole blood by utilizing the concept of incorporating into those liquid controls, mammalian albumin in accordance with the disclosures made herein.

The blood gas control must contain appropriate $O_2$ and $CO_2$ concentrations in order to standardize the test equipment with respect to those gases. The desired $P_{O_2}$ and $P_{CO_2}$ levels are obtained by layering a gas mixture over the buffered liquid medium. The gas is preferably layered over the liquid control of this invention immediately prior to sealing the liquid suspension into ampules or other suitable containers.

Depending on the pH and temperature of the solution, the carbon dioxide can take the form of either a dissolved gas or a hydrated species such as carbonic acid with the associated bicarbonate and carbonate anions.

Since the total gas pressure within the sealed control must be maintained within certain practical limits it is necessary to add bicarbonate ion, preferably in the form of sodium bicarbonate, to ensure a sufficient $P_{CO2}$ level. The sealed control constitutes a closed system with respect to the total amount of $CO_2$ available. Because of this, the pH and $P_{CO2}$ represent an equilibrium between the amount of $CO_2$ in the gas mixture which is layered over the cell suspension, the concentration of bicarbonate or carbonate anion which is added to the buffered solution and the contribution of non-carbonate-derived protons and hydroxyl ions to the pH of the buffered solution.

The range of bicarbonate ion used in the preparation of the control of this invention is about 0.005 to about 0.2 M to ensure that the $P_{CO2}$ is within the desired range. Preferably the added bicarbonate ion is in the concentration range of about 0.01 to about 0.12 M. At the same time the concentration range for $CO_2$ in the gas mixture is about 2 to about 15 % v/v; preferably about 5 to 10% v/v, to maintain an appropriate $P_{CO2}$ in the sealed control.

The $P_{O2}$ is affected by the concentration of oxygen in the gas mixture, the solubility of oxygen in the buffered solution, and the availablity of reduced hemoglobin to bind free oxygen. A suitable concentration range of oxygen useful in the preparation of the controls of this invention is about 2 to about 30% v/v; preferably, about 7 to about 20% v/v. Hence, a suitable composition of a gas mixture to be layered, e.g., in the headspace over the buffered liquid solution of the reference standard of this invention is about 2-30% v/v oxygen and about 2 to about 15% v/v of carbon dioxide, the balance being nitrogen or other inert gas.

Unstabilized erythrocytes in suspension will lose hemoglobin by hemolysis into the suspending liquid medium. Since this cell-free hemoglobin is no longer associated with the enzyme methemoglobin reductase, as it is in the cell, it oxidizes rapidly to methemoglobin. Aside from the adverse cosmetic effect associated with hemolysis, the oxidation of hemoglobin to methemoglobin results in instability of the hemoglobin parameters. To combat this problem, stabilizers can be used. The preferred crosslinking reagent for stabilizing erythrocytes in the practice of this invention is dimethyl adipimidate (DMA). Hydrochlorides of DMA, e.g., dimethyl adipimidate dihydrochloride, are also useful.

Reaction conditions for the reaction of DMA with amines in aqueous solutions are well known. At low pH DMA hydrolyzes. Hence, a large excess of DMA is required in order to provide sufficient DMA to react with the amino groups. In addition, most amino groups are protonated at low pH. This makes them less reactive than the nonprotonated amino groups.

At high pH hydrolysis is suppressed. In general the higher the pH, the lower the concentration of DMA required to imidate the protein, the faster the imidation reaction and the fewer the side reactions of DMA, e.g., hydrolysis.

However, the higher the reaction pH, the greater likelihood there is of damaging the erythrocytes. Hence a balance must be struck between using a high pH for advantageous reaction conditions and limiting the pH level to prevent damage to erythrocytes.

The degree of imidation of erythrocytes is a function of pH, reaction time, and temperature. If imidation is not allowed to progress sufficiently, the erythrocytes will not be stabilized and will lose hemoglobin through hemolysis. On the other hand, if imidation is carried too far the erythrocyte will be excessively hardened. In order to accomplish the hemoglobin tests cell lysis must occur in the test equipment. Hence, imidation must be controlled to avoid both the production of fragile cells susceptible to hemolysis and hardened cells in which lysis cannot occur.

This imidation balance is controlled by fixing the imidation reaction conditions as follows:
1. DMA concentration is maintained at about 0.77 to about 8.00 g/l preferably about 0.85 to about 4.0 g/l e.g. 0.9 g/l
2. The pH of the imidation solution is maintained at about 7.3 to 11.3, preferably about 8 to about 10, more preferably about 8.5 to about 10, most preferably about 8.5 to about 9.5, e.g., about 9.2. The control of pH is best accomplished by the use of inorganic bases such as sodium bicarbonate or sodium carbonate. Amine buffers must be avoided since they will react with the DMA.
3. The reaction time can vary from 15 to 60 minutes, preferably about 18 to about 40 minutes, more preferably about 20 to about 30 minutes, e.g. about 25 minutes.
4. The imidation reaction is carried out at a temperature of about 20° to about 30° C., preferably about 22° to about 28° C., more preferably at about 24° to 26° C., e.g., about 25° C.

Under the foregoing conditions the number of erythrocytes which can be effectively treated will vary from about 133 $10^4$ to about $1 \times 10^7$ per mirco liter. That is, an erythrocyte count of about $1 \times 10^4$ to about $1 \times 10^7$ ul and preferably about $5.8 \times 10^5$ to about $6.2 \times 10^5$ ul, will be used.

The process for stabilizing erythrocytes in accordance with this invention may be summarized as follows:
1. Erythrocytes obtained from outdated human blood are washed in physiological saline, centrifuged and resuspended in a fixing buffer of 0.1 M sodium carbonate and sodium bicarbonate containing sodium chloride;
2. The erythrocyte count is adjusted by adding or removing fixing buffer as necessary;
3. The DMA is added and the reaction is allowed to proceed with stirring;
4. While the reaction is being carried out, either pure oxygen or pure carbon monoxide is bubbled through the cell suspension. The effect of this is to load the intracellular hemoglobin with the appropriate gas so that subsequent reaction of the hemoglobin with DMA fixes the hemoglobin in the oxygen or carbon monoxide carrying conformation, thus "locking" the gas into the hemoglobin and increasing the stability of the $O_2Hb$ and COHb parameters;
5. The stabilized cells are centrifuged to remove the fixing reagents and resuspended in a HEPES-bicarbonate-saline buffer of a pH of 7.13 to lower the pH;
6. Cell populations of the $O_2Hb$ and COHb type are combined on a volumetric basis to achieve the desired control level.
7. The combined cells are centrifuged to remove the HEPES-bicarbonate-saline buffer;

8. The centrifuged cells are resuspended in a final buffer solution in a volume such that the targeted THb is achieved at a pH in the physiological range. The stability of the pH, $P_{O_2}$ and $P_{CO_2}$ depends on preventing the erythrocytes from respiring. To this end the protein-based buffer was formulated to contain no appreciable concentration of nutrients, and erythrocytes are selected so that they are as old as possible in order to allow them to deplete themselves of intracellular nutrients. However, when the cells are so depleted they cannot efficiently reduce methemoglobin, formed in the cells from the spontaneous oxidation of hemoglobin, back to hemoglobin.

Although, in the practice of this invention, most of the hemoglobin is stabilized in the oxy- or carboxyform when the stabilized erythrocytes are prepared, with time, some of these hemoglobins lose their gas despite DMA treatment, and the resultant hemoglobin can be oxidized to methemoglobin. This oxidation process can be retarded by the addition of anti-oxidants, or substances which themselves are preferentially oxidized, thereby stabilizing the control system.

The anti-oxidant compounds suitable for use in the practice of this invention are characterized by the fact that they undergo spontaneous oxidation at a slow rate, have an oxidation potential high enough to afford ready reduction in a biological system and have acceptable olfactory properties. Illustrative, non-limiting examples of these anti-oxidants are dithioerythritol (DTE) and dithiothreitol (DTT) the optical isomer of DTE. The anti-oxidant is utilized at about 0.001 M to about 0.006 M based on the total suspension medium, preferably at about 0.002 M to about 0.005 M, more preferably about 0.003 M to 0.005 M.

A persistent problem in preparing controls which have a long shelf life is microbial contamination. A combination of neomycin and chloroamphenicol adequately preserve the material against bacteria but not against fungus growth. The addition of disodium ethylenediaminetetraacetic acid (EDTA) to the bactericides resulted in anti-fungal activity.

The neomycin sulfate is utilized at about 0.10 to about 0.12 g/l preferably about 0.11 g/l and the chloramphenicol is utilized at about 0.10 to about 0.72 g/l preferably at about 0.15 to about 0.66 g/l more preferably about 0.3 to about 0.4 g/l e.g. about 0.33 g/l.

Typical formulation ranges for the buffered protein solution used in the blood gas control of this invention are:

| Ingredient | Quantity for 1 Liter |
| --- | --- |
| Bovine serum albumin | 40-60 g |
| HEPES buffer | 11.92-16.68 g |
| Sodium bicarbonate | 0.84-10.08 g |
| Sodium chloride | 1.00-3.00 g |
| Dithioerythritol | 0.07-0.77 g |
| Neomycin sulfate | 0.10-0.12 g |
| Chloramphenicol | 0.32-0.34 g |
| Disodium ethylenediamine tetraacetic acid | 0.37-3.72 g |
| Deionized water | Q.S. |

Although it is preferable to include the serum albumin in the composition so that the control will mimic whole blood as closely as possible, the serum albumin may be deleted if it is desired to make a less expensive control.

To ensure the shelf life of the blood gas-hemoglobin analysis control of this invention, the suspending medium for the erythrocytes preferably has an osmolality substantially the same as whole human blood, that is about 280 to 350 mOsm/kg, preferably 320 mOsm/kg±5 mOsm/kg. The osmolality of the solution is adjusted by the addition of sodium chloride to the suspension medium of the control.

While the foregoing description has identified DMA as the preferred protein crosslinking agent it will be evident from this disclosure that any suitable imidoester can be used as the cross-linking agent, e.g. dimethyl suberimidate.

It is, of course, necessary to package the control for storage, shipment and use. While reference will be made to "ampules" throughout this disclosure, it will be evident, from this disclosure, to those skilled in the art, that any liquid impermeable material which can be sealed to be gas tight will suffice. For example, a glass vial having a rubber septum which is sealed so as to be air tight is a suitable container. The rubber septum should be designed so as to be readily cut away for test purposes. As used in the specification and claims, the term "ampule" has its conventional meaning, but includes any suitable container for the control as heretofor described including stoppered vials, foil pouches, etc.

When the control is filled into ampules, head space must be left to introduce the gas mixture which will provide the $P_{O_2}$ and $P_{CO_2}$ parameters. While the ratio of free head space to liquid suspension volume is not critical, ratios of head space volume to liquid volume of greater than 2 should be avoided because the available surface area on the interior of the ampule will be so great as to not permit adequate mixing and handling of the control, in use. Similarly, this ratio can be zero if the cell suspension is pre-equilibrated with the gas mixture prior to sealing of the ampule. It is preferred, however, that the ratio of gas to liquid volume be at least 0.75. Hence, in its preferred embodiment the ampule will be filled with sufficient liquid so that the gas to liquid volume will be about 0.75 to about 2; more preferably about 0.9 to about 1.5, e.g., 1.0.

After the desired amount of cell suspension has been added to the ampule, an oxygen-carbon dioxide-inert gas mixture of the appropriate composition is blown into the ampule to displace the air already occupying the head space. The gas should be layered over the liquid suspension so as to avoid foaming of the suspension. Sufficient time is allowed for displacement of all of the ambient air, and the ampule is sealed at ambient pressure.

In the practice of this invention, during the fixing process, the red blood cell count is the important parameter, since it is the basis for determining the stoichiometric amount of cross-linking agent which is required.

In preparing the controls of this invention, however, the significant parameter is not the cell count but the total hemoglobin content of the cells expressed in grams per deciliter.

The hemoglobin content of the cells can be determined by any of the methods well known to those skilled in the art. For example, a suspension of red blood cells of known cell count is reacted with a cyanide in a solution containing an oxidizing agent and an agent which causes cell lysis. The cyanide derivative of the hemoglobin has a known extinction coefficient. Hence, using a laboratory spectrophotometer, the total hemoglobin content of the sample can be determined.

The advantages of this invention may be more readily appreciated by reference to the following examples. All procedures described are performed asceptically under sterile conditions.

EXAMPLE I

Separation of Erythrocytes from Whole Blood

A unit of outdated whole blood was washed in three washing steps using an IBM Model 2991-1 centrifuge with a 0.9% saline solution. Approximately one liter of wash solution was used in each step. The buffy coat was removed and the washed red blood cells suspended in saline solution.

EXAMPLE II

Fixation of Sterile Blood Cells

In the preparation of oxyhemoglobin and carboxy hemoglobin cells in accordance with this invention a fixing buffer having a pH of 9.2 was prepared using the following formulation:

TABLE I

| Ingredients | Quantity for 5 Liters |
|---|---|
| Sodium carbonate | 7.22 g |
| Sodium bicarbonate | 1.48 g |
| Deionized water | Q.S. |
| Sodium chloride | Q.S. |

In preparing the fixing buffer the pH was adjusted using 0.1 M solutions of sodium carbonate and sodium bicarbonate, the carbonate being used to increase the the pH and the bicarbonate being used to decrease the pH, as required, in order to set the pH value at 9.2±05. Sodium chloride was added to adjust the osmolatity of the solution to 320 mOsm/kg±5 mOsm/kg. Approximately 5g/l of sodium chloride are required.

A. Oxyhemoglobin Cells

Washed red blood cells (RBCs) from one unit of whole blood prepared in the manner described in Example I were suspended in the fixing buffer and the cell count adjusted to $6.0 \times 10^5 \pm 0.2 \times 10^5$ RBCs/ul. Approximately three liters of fixing buffer were required. Solid dimethyl adipimidate dihydrochloride was added so that the concentration of DMA-HCl was 0.9g/l. Oxygen gas was immediately bubbled through the suspension with constant stirring. Stirring and gassing at 25° C. was continued for an incubation period of 25 minutes. At the end of the incubation period the cells were centrifuged and washed in a buffer. The wash buffer composition was as follows:

TABLE II

| Ingredients | Quantity for 2 liters |
|---|---|
| HEPES | 28.56 g |
| Sodium bicarbonate | 3.38 g |
| Deionized water | Q.S. |

The pH of the wash buffer was adjusted to 7.15±0.04 with 5 N NaOH, and the osmolality was adjusted to 320 mOsm/kg±5 mOsm/kg with NaCl (approximately 6g/l). The wash solution was filtered through a stirle 0.22 μm Millipore filter. The washed cells were collected in a bulk bottle.

B. Carboxyhemoglobin Cells

The procedure followed to prepare oxyhemoglobin cells was repeated replacing oxygen with carbon monoxide in order to prepare carboxyhemoglobin cells.

EXAMPLE III

Preparation of Blood Gas—Hemoglobin Analysis Controls

Three blood gas—hemoglobin analysis controls were prepared at three levels to approximate physiological blood conditions: Level I-acidosis; Level II-Normal; and Level III—Alkalosis. For Level II only cells containing oxyhemoglobin were used, however, for Levels I and III a blend of oxyhemoglobin and carboxyhemoglobin cells were used. The composition of the suspending medium for each level is shown in Table III.

TABLE III

| | Quantity for 1 liter | | |
|---|---|---|---|
| Ingredient | Level I | Level II | Level III |
| Bovine serum albumin | 60 g. | 60 g. | 60 g. |
| HEPES buffer | 14.28 g. | 14.28 g. | 14.28 g. |
| Dithioerythritol | 0.154 g. | 0.154 g. | 0.154 g. |
| Neomycin sulfate | 0.110 g. | 0.110 g. | 0.110 g. |
| Chloramphenicol | 0.330 g. | 0.330 g. | 0.330 g. |
| EDTA | 2.23 g. | 2.23 g. | 2.23 g. |
| Sodium Bicarbonate | 0.845 g. | 2.895 g. | 9.10 g. |
| Deionized water | Q.S. | Q.S. | Q.S. |
| Sodium chloride | Q.S. | Q.S. | Q.S. |
| pH | 7.15 ± .04 | 7.4 ± .04 | 7.65 ± 04 |

In each level the pH was adjusted using 5 N NaOH. The osmolality of the solutions was adjusted the 320 mOsm/kg±5 mOsm/kg with approximately 2 g/l of NaCl.

Controls were prepared in 1000 ampule lots for testing. Each ampule of 3 ml was filled with 1.7 ml of material. In preparation of the ampules the blends shown in Table IV were used.

TABLE IV

| | Blood Gas Control Ampule Preparation | | |
|---|---|---|---|
| Ingredient | I | II | III |
| Suspension Medium[1] | 2.9 l[3] | 3.4 l[3] | 3.5 l[3] |
| Oxyhemoglobin Cells[2] | 958 ml[4] | 1.7 l | 1303 ml[4] |
| Carboxyhemoglobin Cells[2] | 217 ml | — | 1050 ml |
| Gas mixture % $O_2$—% $CO_2$, balance $N_2$ | 20-5 | 12-5 | 7-10 |
| $P_{CO_2}$ mmHg | 20 ± 7 | 35 ± 7 | 60 ± 7 |
| $P_{O_2}$ mmHg | 140 ± 10 | 100 ± 10 | 50 ± 10 |
| Total Hemoglobin (g/dl) | 9 ± 1 | 13 ± 1 | 17 ± 1 |
| % Oxyhemoglobin | 83 ± 3 | 96 ± 2 | 63 ± 3 |
| % Carboxyhemoglobin | 15 ± 2 | <5 | 32 ± 3 |
| % Methemoglobin | <3 | <3 | <3 |

[1] Suspension medium as described in Table III.
[2] Prepared as described in Example II A and B.
[3] Approximate values.
[4] Blended from suspensions of the cells in wash solution (Table II). An amount of the carboxyhemoglobin containing cells to be used in selected and the appropriate amount of oxyhemoglobin containing cells is added.

The three levels of controls are intended to cover a control range over which the test equipment is calibrated, e.g. total hemoglobin of 6–20% w/v. A normal level of total hemoglobin is about 12% while a low range (level I) is 8-9% and a high range (level II) is about 18–19%.

The 3 ml ampules were filled with 1.7 ml of suspension. Prior to sealing the ampules were flushed with the appropriate gas mixture to displace all room air. The gas was layered over the liquid without allowing the liquid to foam.

The blood gas-hemoglobin analysis controls were found to have a stability of about 155 to 430 days when stored at 4° C. By comparison, formaldehyde stabilized erythrocytes prepared according to the disclosure of U.S. Pat. No. 3,973,913, modified as described below, have a stability of less than sixty days. The procedure of the '913 patent was modified as follows: (1) no sodium carbonate was added after cells were fixed to adjust $PCO_2$ levels, (2) the final buffer was 0.75 ml HEPES 0.075 M NaCl, pH 7.4, and (3) there was no final adjustment of pH before ampuling. A commercially available product prepared with formaldehyde-fixed erythrocytes was found to have a shelf life of about 60 days.

EXAMPLE IV

Comparison of Protein Cross-Linking Agents

Comparative studies were conducted on controls prepared with cells cross-linked with formaldehyde, sodium tetrathionate, diamide, diethyl oxydiformate and dimethyl suberimidate. Formaldehyde was an effective fixing agent but did not offer the degree of stability achieved with DMA. While dimethyl suberimidate was an effective cross-linking agent there was a greater day-to-day and ampule-to-ampule variation than that found with cells fixed with DMA.

Diamide and sodium tetrathionate fixation procedures were carried out in accordance with the description of Haest, C.W.M., et al, "Intra and Intermolecular Cross-Linking of Membrane Proteins In Intact Erythrocytes and Ghosts by SH-Oxidizing Agents," *Biochem. Biophys. Act.* 469: 226–230 (1977), with the exception of certain modifications. The incubation period was extended to three hours and washing of red blood cells was done with a Haemonetics 15 M cell washing system being substituted for the batch-wise washing process.

Erythrocytes fixed with diamide or sodium tetrathionate were extremely unstable and lysed completely after three weeks at 4° C. or 25° C. Continued storage of lysed cells at 25° C. resulted in gelation of the solution after two months.

In preparing cells stabilized with diethyl oxydiformate the saline suspension medium was replaced with 0.1 M NaCl-0.5 M Tris buffer at a pH of 9.0. Four tenths of a mililiter of diethyl oxydiformate were added to a 125 ml suspension of cells and the mixture stirred for two hours at 25° C.

Controls prepared with diethyl oxydiformate were also unsatisfactory. The $P_{O2}$ was stable for at least five months when the suspension was stored at 4° C. but the day-to-day and ampule-to-ampule variation of the $P_{CO2}$ was unacceptable.

EXAMPLE V

Methemoglobin Stabilization Reagents

The addition of nystatin, lactic acid, cholesterol, sodium fumarate and xylitol did not improve the real time stability of hemoglobin over that of controls containing dithioerythritol. The results are shown in Table V.

TABLE V

| % MetHgb | Methemoglobin Stabilization Stabilizer | Initial[1] | 175 Days[1] |
|---|---|---|---|
| 1. | Nystatin | 0.1 | 4.0 |
| 2. | Xylitol | 0.2 | 4.8 |
| 3. | Fumarate | 0.3 | 5.8 |

TABLE V-continued

| % MetHgb | Methemoglobin Stabilization Stabilizer | Initial[1] | 175 Days[1] |
|---|---|---|---|
| 4. | Cholesterol | 1.4 | 3.4 |
| 5. | Lactate | 0.3 | 3.1 |
| 6. | Control | 0.4 | 5.9 |
| 7. | Dithioerythritol | 0.3 | 2.5[2] |

[1] values are averages of three determinations,
[2] values obtained at 196 days.

It will be evident to those skilled in the art who refer to this disclosure that the products of this invention are most suitably distributed in kit form. Preferably, the kit contains at least one ampule at each level (acidosis, normal and alkalosis) of control. The physiological pH ranges for each level are: acidosis—7.0 to 7.3; normal—7.4±0.1; alkalosis—7.6±0.1.

The terms "stabilized oxyhemoglobin containing erythrocytes" and "stabilized carboxyhemoglobin containing erythrocytes" means erythrocytes stabilized in accordance with the method of this invention wherein the gas with which the erythrocytes are associated during stabilization is oxygen and carbon monoxide respectively. It is understood that throughout the specification and claims reference to hemoglobin, oxyhemoglobin and carboxyhemoglobin refers to such species contained within the erythrocyte unless otherwise specified.

The invention being thus described, it will be obvious that the same may be varied in many ways. Such variations are not to be regarded as a departure from the spirit or scope of the invention and all such modifications are intended to be included within the scope of the claims.

What is claimed is:

1. A process for stabilizing mammalian erythrocytes for use in a blood gas-hemoglobin analysis control whereby specific hemoglobin values for oxyhemoglobin, carboxyhemoglobin and methemoglobin are maintained which comprises:
   (a) suspending said erythrocytes in a buffered fixing medium comprising a water solution of a buffering agent, said medium having a pH of about 7.3 to about 11.3;
   (b) contacting the erythrocytes with a gas, wherein the gas is, oxygen or carbon monoxide in the presence of a protein cross-linking agent at a temperature 20° C. to about 30° C. for a reaction time of about 15 minutes to about 60 minutes; and
   (c) recovering the stabilized erythrocytes.

2. The process according to claim 1 wherein the erythrocyte is a human erythrocyte.

3. The process according to claim 1 wherein the protein cross-linking agent is an imidoester.

4. The process according to claim 3 wherein the imidoester is dimethyl adipimidate or dimethyl suberimidate.

5. The process according to claim 1 where the pH of the fixing medium is about 8 to about 10.

6. The process according to claim 1 wherein the gas is oxygen.

7. The process according to claim 1 wherein the buffering agent is an alkali metal carbonate, an alkali metal bicarbonate or a mixture thereof.

8. The process according to claim 1 wherein the fixing medium has an osmolality substantially the same as that of human blood.

9. The process according to claim 1 wherein the erythrocytes are present in the fixing medium at a count of about $1\times 10^4$ to about $1\times 10^7/\mu l$.

10. The process according to claim 4 wherein the dimethyl adipimidate is present at about 0.77 to about 8.0 g/l.

11. The process according to claim 1 wherein the erythrocyte is a human erythrocyte, the pH of the fixing medium is about 8 to about, 10, the protein cross linking agent is dimethyl adipimiate present in the fixing medium at a concentration of about 0.85 to about 4.0 g/l and the reaction is carried out at a temperature of about 23° C. to about 28° C. for about 18 to about 40 minutes.

12. A stabilized erythrocyte prepared according to the process of claim 1.

13. A blood gas-hemoglobin analysis control product comprising:
   (a) a buffered suspension medium comprising a water solution of a buffering agent, said medium having a pH of about 6.8 to about 8.0; and
   (b) stabilized erythroctes prepared according to the process of claim 1, said erythrocytes being present in the suspension medium in an amount such that the suspension medium has a total hemoglobin concentration of about 3 to about 24 g/dl; said hemoglobn comprising about 60 to 100% oxyhemoglobn and about 0 to 35% (w/w) carboxyhemoglobin.

14. The product according to claim 13 wherein the suspension medium contains a serum albumin.

15. The product according to claim 14 wherein the serum albumin is bovine serum albmin present at about 40 to about 60 grams per liter of suspension medium.

16. The product according tb claim 13 wherein the buffering agent is a mixture of an amine buffer and sodium bicarbonate, and the amine buffer is at least one of N-(tris hydroxymethyl)methl-2-amino-ethonesulfonic acid and N-2-hydroxyethyl piperazine-N-2-ethonesulfonic acid.

17. The product according to claim 13 wherein the suspension medium contains dithioerythritol at a concentration of about 0.07 to about 0.77 grams per liter of suspension medium.

18. The product according to claim 13 wherein the suspension medium contains neomycin sulfate at about 0.10 to about 0.12 grams per liter of suspension medium, about 0.32 to about 0.34 grams of chloramphenicol per liter of suspension medium and about 0.37 to about 3.72 grams of disodium ethylenediaminetetraacetic acid.

19. The product according to claim 13 wherein the the erythrocytes are selected from the group consisting of: oxyhemoglobin-containing erythrocytes, carboxyhemoglobin-containing erythrocytes, and mixtures thereof.

20. The product according to claim 13, which is sealed in an ampule, the atmosphere in said ampule comprising oxygen, carbon dioxide and an inert gas, the oxygen having a partial pressure of about 20 to 400 mm Hg and the carbon dioxide having a partial pressure of about 10 to about 75 mm Hg.

21. The product of claim 20 wherein the erythrocytes comprise a blend of stabilized erythrocytes which are a mixture of stabilized oxyhemoglobin- and carboxyhemoglobin-containing erythrocytes.

22. A lit comprising at least two ampules at different H ranges of the product accordng to claim 13.

* * * * *